United States Patent [19]
Webster

[11] Patent Number: 6,034,076
[45] Date of Patent: Mar. 7, 2000

[54] STABLE HYDRATES OF A CEPHALOSPORIN CHLORIDE SALT

[75] Inventor: Richard Andrew Bentely Webster, Dover, United Kingdom

[73] Assignee: Pfizer Inc., New York, N.Y.

[21] Appl. No.: 08/894,123

[22] PCT Filed: Feb. 19, 1996

[86] PCT No.: PCT/GB96/00373

§ 371 Date: Aug. 14, 1997

§ 102(e) Date: Aug. 14, 1997

[87] PCT Pub. No.: WO96/26209

PCT Pub. Date: Aug. 29, 1996

[30] Foreign Application Priority Data

Feb. 24, 1995 [GB] United Kingdom .................. 9503717

[51] Int. Cl.$^7$ ....................... A61K 31/545; C07D 501/36
[52] U.S. Cl. ............................................ 514/203; 540/225
[58] Field of Search ............................... 544/225; 514/203

[56] References Cited

U.S. PATENT DOCUMENTS

| | | | |
|---|---|---|---|
| 4,035,361 | 7/1977 | Wheeler | 424/246 |
| 4,146,710 | 3/1979 | Naito | 544/27 |
| 4,258,050 | 3/1981 | Harbridge | 424/272 |
| 4,888,344 | 12/1989 | Sunagawa | 514/210 |

FOREIGN PATENT DOCUMENTS

| | | |
|---|---|---|
| 416814 | 3/1991 | European Pat. Off. . |
| 638573 | 2/1995 | European Pat. Off. . |

*Primary Examiner*—Mark L. Berch
*Attorney, Agent, or Firm*—Peter C. Richardson; Paul H. Ginsburg; Lorraine B. Ling

[57] ABSTRACT

The cephalosporin compound [6R, 7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride is provided as a mono-, di- or tri-hydrate. The hydrates are produced by treating an aqueous solution of the corresponding carboxylate with hydrogen chloride and have been found to possess unexpectedly superior stability properties over other forms of the compound. The hydrates may be used in the treatment and/or prevention of bacterial infections in humans and animals.

3 Claims, No Drawings

STABLE HYDRATES OF A CEPHALOSPORIN CHLORIDE SALT

This application is a filing under 35 U.S.C. 371 of International Application No. PCT/GB96/00373.

The present invention relates to a novel compound, to a process for its manufacture and to its use in the treatment and/or prevention of bacterial infections in humans and animals caused by a wide range of organisms.

EP-A-0416814 (Beecham Group plc) describes certain cephalosporin compounds which are described to be useful in the treatment of bacterial infections in humans and animals caused by a wide range of organisms.

One particular compound mentioned therein, i.e., [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylate (i.e., example 2) has now been prepared as crystalline carboxylic acid chloride hydrochloride mono-, di- or tri-hydrate.

This particular form of the compound has unexpectedly superior stability properties over the freeze dried material of example 2 in EP-A-0416814.

EP-A-0638573 discloses crystalline hydrates of the cephalosporin 7[(Z)-2-(2-aminothiazole-4-yl)-2-(2-carboxylprop-2-oxyimino)acetamido]-3-(5-methyl- 1,4,6-triaminopyrimidinium-2-yl)thiomethyl-3-cephem-4-carboxylate.

U.S. Pat. No. 4146710 teaches a crystalline cephalosporin derivative which is a dihydrochloride (or dihydrobromide) which may be hydrated up to the hexahydrate.

Accordingly the present invention provides [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride as a mono-, di- or tri-hydrate.

Preferably the present invention provides [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride as a tri-hydrate.

The present invention further provides a process for the preparation of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride as a mono, di or tri-hydrate said process comprising treating an aqueous solution of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylate with hydrogen chloride.

Suitably [6R,7R]-7-[2-(2-Amino-4-thiazolyl)-2-(Z)-(methoxyimino) acetamido]-3-[1-(methylamino)pyridinium-4-thiomethyl]-ceph-3-em-4-carboxylate is dissolved in water and treated with aqueous hydrochloric acid for example a 2 molar solution thereof. The resulting solution is suitably diluted with a water soluble organic solvent to precipitate the product; for example tetrahydrofuran. The resulting mixture may then be cooled for example overnight to 0 to 5° C., suitably at around 4° C. The resulting crystalline product may then be isolated for example by filtration, and dried for example in vacuo at ambient temperature.

It should be appreciated that more rigorous drying conditions will remove the bound molecules of water of hydration. In this way drying conditions may be conventionally controlled to give [6R,7R]-7-[2-(2-Amino-4-thiazolyl)-2-(Z)(methoxyimino)acetamido]-3-[1-(methylamino)pyridinium-4-thiomethyl]-ceph-3-em-4-carboxylic acid chloride hydrochloride as the mono, di or tri-hydrates.

[6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxy may be prepared according to the procedures mentioned in or outlined by EP-A-416 814.

It should be appreciated that [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride mono, di or tri-hydrate is an active medicinal product and may be formulated into unit dose forms suitable for administration to humans or animals in need of treatment.

[6R,7R]-7-[2-(2-Amino-4-thiazolyl)-2-(Z)-(methoxyimino)acetamido]-3-(methylamino)pyridinium-4-thiomethyl]-ceph-3-em-4-acid chloride hydrochloride mono, di or tri-hydrate is especially suitable for the treatment and/or prevention of bacterial diseases in animals.

Such unit dose forms may be for example those contemplated in EP-A-416 814 and those generally known in the art, especially those particularly adapted for administration to animals.

Amounts of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride mono, di or tri-hydrate suitable for formulation into a unit dose form and the number of unit dose forms administered to a human or animal patient is mentioned in EP-A-0 416 814 and is hereincorporated by reference.

The types of bacterial infections which may be treated by [6R,7R]-7-[2-(2-Amino-4thiazolyl)-2-(Z)-(methoxyimino)acetamido]-3-[1-(methylamino)pyridinium-4-thiomethyl]-ceph-3-em-4-carboxylic acid chloride hydrochloride mono, di or trihydrate include those specifically mentioned in EP-A-416 814 which are incorporated herein by reference. Such infections are hereinafter referred to as "the infections".

The present invention therefore provides a method for the treatment and/or prevention of "the infections" which comprises administering an effective amount of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylic acid chloride hydrochloride mono, di or tri-hydrate to a sufferer in need thereof.

The present invention also provides the use of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylicacid chloride hydrochloride mono, di or tri-hydrate in the treatment and/or prevention of "the infections" in humans or animals.

The present invention also provides the use of [6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylicacid chloride hydrochloride mono, di or tri-hydrate in the manufacture of a medicament for treating and/or preventing "the infections" in humans or animals.

The present invention also provides a pharmaceutical composition for use in the treatment and/or prevention of "the infections" in animals or humans which comprises admixing [6R,7R]-7-[2-(2-Amino-4-thiazolyl)-2-(Z)-(methoxyimino)acetamido]-3-[1-(methylamino)pyridinium-4-thiomethyl]-ceph-3-em-4-acid chloride hydrochloride mono, di or tri-hydrate with pharmaceutically acceptable excipients.

The following example illustrates the present invention.

Example 1

[6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylicacid chloride trihydrate

[6R,7R]-7-[2-(2-Amino-4-thiazolyl)-2-(Z)-(methoxyimino)acetamido]-3-[1-(methylamino)pyridinium-4-thiomethyl]-ceph-3-em-4-carboxylate (2.75 g, 5.1 mmol) was dissolved in H$_2$O (10 mL) and acidified with 2M aqueous HCl (15 mL). The solution was diluted with THF (400 mL) and the mixture stored at 4° C. overnight. The resulting crystalline material was collected by filtration, washed with TBF (100 mL) and dried in vacuo at 20° C. The title compound (2.7 g) was isolated as a crystalline solid (needles): δ (DMSO-d6) 2.99(s, 3H), 3.55(d, J=18 Hz, 1H), 3.80(d, J=18 Hz, 1H), 3.95(s, 3H), 4.41(q, J=12.9 Hz, 2H), 5.24(d, J=4.8 Hz, 1H), 5.79(d.d, J=7.9 Hz, 4.8 Hz, 1H), 6.96(s, 1H), 8.01(d, J=7.3 Hz, 2H), 8.92(d, J=7.2 Hz, 2H), 9.87(d, J=7.9 Hz, 1H); $H_2O$ 8.9% (Theory 8.16%).

I claim:

1. A compound comprising: [6R, 7R]-7-[2-(2-Amino-4-tiazolyl)-2-(Z)-(methoxyimino)acetamido]-3-[1-(methylamino)pyridinium-4-thiomethyl]-ceph-3-em-4-carboxylic acid chloride hydrochloride as a trihydrate.

2. A process for the preparation of [6R, 7R]-7-[2-(2-amino-4-thiazolyl)-2-(Z)-(methoxyimino)acetamido]-3-[1-(methylamino)pyridinium-4-thiomethyl]-ceph-3-em-4-carboxylic acid chloride hydrochloride tri-hydrate, said process comprising treating an aqueous solution of [6R, 7R]-7-[2-(2-amino-4-thiazolyl)-2-(Z)-(methoxyimino) acetamido]-3-[1-(methylamino) pyridinium-4-thiomethyl]-ceph-3-em-4-carboxylate with hydrogen chloride.

3. A method for the treatment and/or prevention of bacterial infections in humans or animals which comprises administering an effective amount of [6R, 7R]-7-[2-(2-amino-4-thiazolyl)-2-(Z)-(methoxyimino)acetamido]-3-[1-(methylamino)pyridinium-4-thiomethyl]-ceph-3-em-4-carboxylic acid chloride hydrochloride tri-hydrate to a sufferer in need thereof.

* * * * *